(12) United States Patent
Sham et al.

(10) Patent No.: US 11,491,146 B2
(45) Date of Patent: Nov. 8, 2022

(54) THERAPEUTIC METHODS AND COMBINATIONS

(71) Applicants: Yuk Yin Sham, Minneapolis, MN (US); Ramaiah Muthyala, Minneapolis, MN (US); Woo-Shik Shin, Minneapolis, MN (US)

(72) Inventors: Yuk Yin Sham, Minneapolis, MN (US); Ramaiah Muthyala, Minneapolis, MN (US); Woo-Shik Shin, Minneapolis, MN (US)

( * ) Notice: Subject to any disclaimer, the term of this patent is extended or adjusted under 35 U.S.C. 154(b) by 0 days.

(21) Appl. No.: 16/014,438

(22) Filed: Jun. 21, 2018

(65) Prior Publication Data
US 2018/0369217 A1    Dec. 27, 2018

Related U.S. Application Data

(60) Provisional application No. 62/524,297, filed on Jun. 23, 2017.

(51) Int. Cl.
| | | |
|---|---|---|
| *A61K 31/4412* | (2006.01) | |
| *A61P 31/04* | (2006.01) | |
| *A61K 31/44* | (2006.01) | |
| *A61K 45/06* | (2006.01) | |
| *A61K 31/43* | (2006.01) | |

(52) U.S. Cl.
CPC .......... *A61K 31/4412* (2013.01); *A61K 31/44* (2013.01); *A61P 31/04* (2018.01); *A61K 31/43* (2013.01); *A61K 45/06* (2013.01); *A61K 2300/00* (2013.01)

(58) Field of Classification Search
CPC ................ A61K 2300/00; A61K 31/43; A61K 31/4412; A61K 45/06; A61P 31/04
See application file for complete search history.

(56) References Cited

FOREIGN PATENT DOCUMENTS

WO    WO-2013101600 A1 *   7/2013   ........... C07D 213/82

OTHER PUBLICATIONS

Muthyala et al., Bioorganic & Medicinal Chemistry Letters vol. 25, Issue 19, Oct. 1, 2015, pp. 4320-4324, (Year: 2015).*
Das Gupta et al., Clin Transl Immunology. Jan. 2016; 5(1): e62, (Year: 2016).*
Mulvey et al., Emerg Infect Dis. Jan. 2011; 17(1): 103-106. (Year: 2011).*
Van der Bij et al., International Journal of Antimicrobial Agents 37 (2011) 513-518 (Year: 2011).*
Fujitani et al., Chest 2011; 139(4):909-919. (Year: 2011).*
Mombelli et al, JID 2011:204, pp. 1367-1374 (Year: 2011).*
CDC, Nov. 24, 2010, (Year: 2010).*
Chiem et al., Antimicrobial Agents and Chemotherapy, Sep. 2015 vol. 59 No. 9, pp. 5851-5853 (Year: 2015).*
Bush et al., Antimicrob Agents Chemother. Mar. 2010; 54(3): 969-976 (Year: 2010).*
Falconer et al., ACS Infect. Dis. 2015, 1, 11, 533-543, (Year: 2015).*
Chan et al., PNAS, Mar. 7, 2017, vol. 114, No. 10, pp. 2717-2722, (Year: 2017).*
Kahraman et al., Open Journal of Bacteriology, published Feb. 20, 2017. (Year: 2017).*
Brem, et al., "Structural Basis of Metallo-β-Lactamase Inhibition by Captopril Stereoisomers", Antimicrob Agents Chemother 60, 142-150 (2016).
Drawz, et al., "New β-lactamase inhibitors: a therapeutic renaissance in an MDR world", Antimicrob Agents Chemother 58(4), 1835-1846(2014).
Han, et al., "Study on the Active Principle of Polyalthia Nemoralis I . The Isolation and Identification of Natural Zinc Compound", Acta Chimica Sinica 39(5), 433-437 (1981). [English Abstract].
Heinz, et al., "Coordination Geometries of Metal Ions in D- or L-Captopril-inhibited Metallo-β-lactamases", J Biol Chem 278, 20659-20666 (2003).
Jacobsen, et al., "The Design of Inhibitors for Medicinally Relevant Metalloproteins", J ChemMedchem 2, 152-171 (2007).
Krenn, et al., "Antiviral Activity of the Zinc Ionophores Pyrithione and Hinokitiol against Picornavirus Infections", J Virol 83, 58-64 (2009).
Marcheselli, et al., "Novel antifouling agent-zinc pyrithione: stress induction and genotoxicity to the marine mussel Mytilus galloprovincialis", Aquat Toxicol 102, 39-47 (2011).
Muthyala, et al., "Cell permeable vanX inhibitors as vancomycin re-sensitizing agents", Bioorganic & Medicinal Chemistry Letters 24, 2535-2538 (2014).
Muthyala, et al., "Discovery of 1-hydroxypyridine-2-thiones as selective histone deacetylase inhibitors and their potential application for treating leukemia", Bioorganic & Medicinal Chemistry Letters 25, 4320-4324 (2015).
Palzkill, "Metallo-β-lactamase structure and function", Ann N Y Acad Sci 1277, 91-104 (2013).
Qiu, et al., "Zinc ionophores pyrithione inhibits herpes simplex virus replication through interfering with proteasome function and NF-κB activation", Antivir Res 100, 44-53 (2013).
Schwartz, et al., "Comparative evaluation of antidandruff clinical efficacy of a potentiated zinc pyrithione shampoo and a zinc pyrithisone/climbazole combination formula", J Am Acad Dermatol 68(4), Supplment 1, p. AB46, P6172 (2013).
Shin, et al., "Discovery of 1-Hydroxypyridine-2(1H)-thione-6-carboxylic Acid as a First-in-Class Low-Cytotoxic Nanomolar Metallo β-Lactamase Inhibitor", ChemMedchem 12(11), 845-849 (2017).
Tailler, et al., "Antineoplastic activity of ouabain and pyrithione zinc in acute myeloid leukemia", Oncogene 31, 3536-3546 (2012).
Zhou, et al., "Stability and in vitro absorption of captopril, enalapril and lisinopril across the rat intestine", Biochem Pharmacol 47, 1121-1126 (1994).

* cited by examiner

*Primary Examiner* — Jean P Cornet
(74) *Attorney, Agent, or Firm* — Viksnins Harris Padys Malen LLP

(57) ABSTRACT

Combinations comprising substituted 1-hydroxypyridine-2 (1H)-thiones or a pharmaceutically acceptable salt thereof and an antibacterial agent are disclosed. Also disclosed are therapeutic methods comprising the administration of a substituted 1-hydroxypyridine-2(1H)-thione or a pharmaceutically acceptable salt thereof and an antibacterial agent.

20 Claims, 5 Drawing Sheets

THERAPEUTIC METHODS AND COMBINATIONS

RELATED APPLICATIONS

This application claims priority to U.S. Provisional Application No. 62/524,297, filed on Jun. 23, 2017. The entire contents of the application referenced above is hereby incorporated by reference herein.

BACKGROUND

Combination antibacterial therapy with β-lactamase inhibitors, remains a viable strategy for overcoming β-lactam drug resistance. With the recent approval of Avibactam, there are currently four β-lactamase inhibitors available for combination antibacterial therapy with β-lactam antibiotics (S. M. Drawz, et al., Antimicrob Agents Ch, 58 (2014) 1835-1846). With the continuing emergence of β-lactam drug resistance worldwide, the discovery of other β-lactamase inhibitors remains an urgent area of research.

Expression of β-lactamase from innate or acquired bla gene is the leading mechanism of β-lactam drug resistance. β-lactamase enzymatically cleaves the β-lactam ring, rendering the β-lactam antibiotics inactive. Based on their mechanistic action of hydrolysis, β-lactamases are commonly referred to as serine (class A, C and D) or metallo β-lactamase (MBLs) (class B) (T. Palzkill, Ann Ny Acad Sci, 1277 (2013) 91-104). IMP, VIM and NDM belong to the subclass B1 of the metallo β-lactamase, consisting of dinuclear zinc metal cofactors necessary for enzyme catalysis. There is currently a lack of lead compounds with optimal therapeutic potential against MBLs available for development. To identify novel classes of metallo β-lactamase inhibitors (MBLi), VIM2, a carbapenemase commonly found in clinical isolates of ESKAPE pathogens was used, as the biochemical screening platform for MBLi discovery.

L-Captopril is an angiotensin converting enzyme inhibitor approved by the FDA for the treatment of hypertension and congestive heart failure. For over a decade, L-captopril and its stereoisomer have been shown to exhibit broad spectrum inhibitory activity against various MBLs (U. Heinz, et al., J Biol Chem, 278 (2003) 20659-20666; J. Brem, et al., Antimicrob Agents Chemother, 60 (2016) 142-150). Its inhibitory potency stems from its thiol group which is viewed as a pharmacological liability for a non-specific zinc binding against other metallo enzymes and is prone to inactivation by metabolic oxidation (X. H. Zhou, et al., Biochem Pharmacol, 47 (1994) 1121-1126). To-date, captopril's use has been limited to the laboratory for improving the understanding of MBL inhibition in antibacterial discovery. Recent structural characterization of Captopril stereoisomer against IMP-1, BcII, and VIM-2 have shown common mode of binding involving a bridge chelation between deprotonated thiolate ion with the two zinc ions (J. Brem, et al., Antimicrob Agents Chemother, 60 (2016) 142-150.). To achieve unique nanomolar inhibition against VIM2 as compared to other MBLs, a salt bridge interaction between its carboxylate to the ionized Arg205 and hydrogen bonding to N210 sidechain is essential. Identifying a novel scaffold which replaces the thiol as the zinc binding group (ZBG) would provide a significant advance in the design of potent MBLi.

1-Hydroxypyridine-2-thione (1,2-HPT), also referred to as pyrithione, is a heterocyclic thiohydroxamic acid (F. E. Jacobsen, et al., J Chemmedchem, 2 (2007) 152-171) that forms a five-membered complex via their oxygen and sulfur atoms with zinc. Zinc pyrithione (ZPT), 2a, can be isolated from Chinese herbal roots *Polyalthia nemoralis* (J. Z. Yao, et al., Acta Pharmaceutica Sinica, 29 (1994) 845-850) and has been shown to possess a broad range of antimicrobials activities (M. Marcheselli, et al., Aquat Toxicol, 102 (2011) 39-47; M. Tailler, et al., Oncogene, 31 (2012) 3536-3546; R. Muthyala, et al., Bioorganic & medicinal chemistry letters, 25 (2015) 4320-4324; G. Y. Han, et al., Acta Chimica Sinica, 39 (1981) 433-437; M. Qiu, et al., Antivir Res, 100 (2013) 44-53; B. M. Krenn, et al., J Virol, 83 (2009) 58-64; J. Schwartz, et al., J Am Acad Dermatol, 68 (2013) Ab46-Ab46). Most recently, compounds with the 1,2-HPT moiety as zinc specific chelating inhibitors of VanX for the re-sensitization of vancomycin against vancomycin resistant *Enterococcus faecium* (VREF) (R. Muthyala, et al., Bioorganic & medicinal chemistry letters, 24 (2014) 2535-2538) and as selective inhibitors of HDAC8 for their potential treatment of leukemia (R. Muthyala, et al., Bioorganic & medicinal chemistry letters, 25 (2015) 4320-4324) have been reported. These earlier successes against zinc enzymes, in particular in its selectivity, have prompted further exploration of the application 1,2-HPT as potential MBLi for overcoming □-lactam drug resistance in ESKAPE pathogens. For comparison purposes, L-captopril and other representative compounds consisting of the hydroxamic and cyclic hydroxamic acid moieties as alternative ZBGs were included (FIG. 1).

Accordingly, there is a need for therapeutic methods and combinations that treat or prevent bacterial infections including drug-resistant bacterial infections. There is also need for therapeutic methods and combinations that treat or prevent bacterial infections that are less toxic. There is also a need for therapeutic agents, methods and combinations that restore the activity of beta lactam antibiotics.

SUMMARY OF INVENTION

One embodiment provides a method for treating or preventing a bacterial infection in an animal (e.g., a mammal such as a human) comprising administering to the animal (a) a substituted 1-hydroxypyridine-2(1H)-thione or a pharmaceutically acceptable salt thereof, and (b) an antibacterial agent or a pharmaceutically acceptable salt thereof.

One embodiment provides a combination of (a) a substituted 1-hydroxypyridine-2(1H)-thione or a pharmaceutically acceptable salt thereof, and (b) an antibacterial agent or a pharmaceutically acceptable salt thereof.

One embodiment provides a kit comprising (a) a substituted 1-hydroxypyridine-2(1H)-thione or a pharmaceutically acceptable salt thereof, (b) an antibacterial agent or a pharmaceutically acceptable salt thereof (c) a container, and (d) a package insert or label indicating the administration of (a) and (b).

One embodiment provides a combination of (a) a substituted 1-hydroxypyridine-2(1H)-thione or a pharmaceutically acceptable salt thereof, and (b) an antibacterial agent or a pharmaceutically acceptable salt thereof for the prophylactic or therapeutic treatment of a bacterial infection.

One embodiment provides the use of (a) a substituted 1-hydroxypyridine-2(1H)-thione or a pharmaceutically acceptable salt thereof, and (b) an antibacterial agent or a pharmaceutically acceptable salt thereof for the preparation of a medicament for the prophylactic or therapeutic treatment of a bacterial infection in an animal (e.g., a mammal such as a human).

One embodiment provides a kit comprising (a) a substituted 1-hydroxypyridine-2(1H)-thione or a pharmaceutically acceptable salt thereof, (b) an antibacterial agent or a pharmaceutically acceptable salt thereof (c) a container, and (d) a package insert or label indicating the administration of (a) and (b) for the prophylactic or therapeutic treatment of a bacterial infection in an animal (e.g., a mammal such as a human).

DETAILED DESCRIPTION

Figure 1:
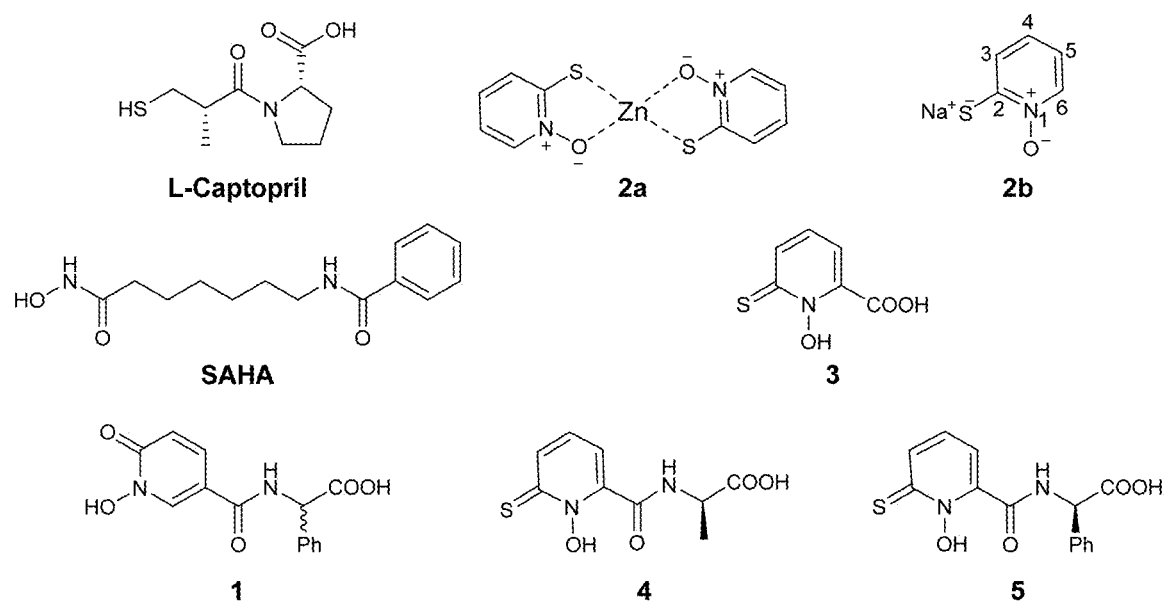
FIG. 1 shows the structures of L-Captopril, SAHA, 1-hydroxypyridine-2(1H)-ones (1) and 1-hydroxypyridine-2 (1H)-thiones analogues (2-5).

The following definitions are used, unless otherwise described.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to the lessening of an undesired physiological change or disorder, such as, for example, the development or spread of a bacterial infection. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. Thus the term treat as described above does not include prevention.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "patient" as used herein refers to any animal including mammals such as humans, higher non-human primates, rodents, domestic and farm animals such as cows, horses, pigs, sheep, dogs and cats. In one embodiment, the patient is a human patient. In one embodiment, the mammal is a human. In one embodiment, the patient is a human patient.

The phrase "therapeutically effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "package insert" is used to refer to instructions customarily included in commercial packages of therapeutic products, that contain information about the indications, usage, dosage, administration, contraindications and/or warnings concerning the use of such therapeutic products.

Substituted 1-hydroxypyridine-2(1H)-thiones

The term substituted 1-hydroxypyridine-2(1H)-thiones as used herein includes compounds that comprise a 1-hydroxypyridine-2(1H)-thione core that is further substituted with one or more (e.g., 1, 2, 3, 5 or 5) substituents. It is to be understood that the 1-hydroxypyridine-2(1H)-thione can exist in any tautomeric form any charged form and any salt form.

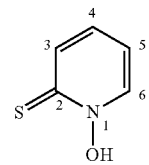

In one embodiment the substituted 1-hydroxypyridine-2 (1H)-thione is substituted at the 6-position with a substituent. In one embodiment the substituted 1-hydroxypyridine-2(1H)-thione is substituted at the 6-position and not substituted at the 3, 4 and 5 positions. In one embodiment the substituted 1-hydroxypyridine-2(1H)-thione is substituted at the 6-position with a substituent and optionally substituted at the 3, 4 and 5 positions with a substituent. In one embodiment the substituted 1-hydroxypyridine-2(1H)-thione is substituted at the 6-position with an acid (—$CO_2H$) and optionally substituted at the 3, 4 and 5 positions with a substituent. In one embodiment the substituted 1-hydroxypyridine-2(1H)-thione is substituted at the 6-position with an acid (—$CO_2H$) and not substituted at the 3, 4 and 5 positions.

As used herein the term substituent includes acid (—$CO_2H$), halogen (e.g., F, Cl. Br and I), CN, ($C_1$-$C_6$)alkyl, —O($C_1$-$C_6$)alkyl, and —C(=O)$NR^1R^2$, wherein each $R^1$ and $R^2$ is independently hydrogen, ($C_1$-$C_6$)alkyl, wherein any ($C_1$-$C_6$)alkyl is optionally substituted with one or more halogen, —$CO_2H$ or phenyl. The term "alkyl" as used herein refers to a saturated linear or branched-chain hydrocarbon radicals.

Antibacterial Agents

Antibacterial agents useful in the methods, combinations, and uses described herein include β-lactam antibiotics or a pharmaceutically acceptable salts thereof. Such antibacterial agents include but are not limited to Amoxicillin, Ampicillin, Methicillin, Piperacillin, Imipenem, Ceftazidime, Piperacillin. Additional antibacterial agents can also be useful in the methods, combinations, and uses described herein. Such antibacterial agents include but are not limited to glycopeptides, aminoglycoside, fluoroquinolones, polymyxins, rifamycins, lipiarmycins, quinolones, sulfonamides, macrolides, lincosamides, tetracyclines, cyclic lipopeptides, glycylcyclines, oxazolidinones, lipiarmycins.

β-Lactamase Inhibitors

The inclusion of additional β-lactamase inhibitors can also be useful in the methods, combinations, and uses described herein. Such β-lactamase inhibitors include but are not limited to Sulbactam, Tazobactam, Clavulanic acid, and Avibactam.

Treatment or Prevention of Bacterial Infections

The treatment or prevention of bacterial infections as described herein include but are not limited to infections that are caused by pathogen that express or overexpress a metallo β-lactamase. Such pathogens include ESKAPE pathogens. ESKAPE pathogens include *Enterococcus faecium, Staphylococcus aureus, Klebsiella pneumoniae, Acinetobacter baumannii, Pseudomonas aeruginosa*, and *Enterobacter* species.

Specific embodiments listed below are for illustration only; they do not exclude other defined embodiments or values or other values within defined ranges. It is to be understood that two or more embodiments may be combined.

In one embodiment the substituted 1-hydroxypyridine-2(1H)-thione or a pharmaceutically acceptable salt thereof is an optionally substituted 6-substituted-1-hydroxypyridine-2(1H)-thione or a pharmaceutically acceptable salt thereof.

In one embodiment the substituted 1-hydroxypyridine-2(1H)-thione or a pharmaceutically acceptable salt thereof is an optionally substituted 1-hydroxypyridine-2(1H)-thione-6-carboxylic acid or a salt thereof.

In one embodiment the substituted 1-hydroxypyridine-2(1H)-thione or a pharmaceutically acceptable salt thereof is 1-hydroxypyridine-2(1H)-thione-6-carboxylic acid or a salt thereof.

In one embodiment the substituted 1-hydroxypyridine-2(1H)-thione or a pharmaceutically acceptable salt thereof comprises a group that forms a salt bridge interaction to R105 of VIM2.

In one embodiment the substituted 1-hydroxypyridine-2(1H)-thione or a salt thereof is an inhibitor of β-lactamase.

In one embodiment the β-lactamase is a metallo β-lactamase.

In one embodiment the metallo β-lactamase is a B1 metallo β-lactamase.

In one embodiment the metallo β-lactamase is IMP, VIM, or NDM.

In one embodiment the metallo β-lactamase is VIM2 or NDM-1.

In one embodiment the metallo β-lactamase is VIM2.

In one embodiment the metallo β-lactamase is NDM-1.

In one embodiment the antibacterial agent or a pharmaceutically acceptable salt thereof is a β-lactam antibiotic or a pharmaceutically acceptable salt thereof.

In one embodiment the antibacterial agent or a pharmaceutically acceptable salt thereof is amoxicillin.

In one embodiment the bacterial infection is a multi-drug resistant bacterial infection.

In one embodiment the bacterial infection is caused by a pathogen that expresses a metallo β-lactamase.

In one embodiment the bacterial infection is caused by a pathogen which overexpresses a metallo β-lactamase.

In one embodiment the bacterial infection is caused by one or more ESKAPE pathogens (*Enterococcus faecium, Staphylococcus aureus, Klebsiella pneumoniae, Acinetobacter baumannii, Pseudomonas aeruginosa*, or *Enterobacter* species).

In one embodiment the animal is a mammal.

In one embodiment the animal is a human.

In one embodiment (a) a substituted 1-hydroxypyridine-2(1H)-thione or a pharmaceutically acceptable salt thereof, and (b) an antibacterial agent or a pharmaceutically acceptable salt thereof are administered separately.

In one embodiment (a) a substituted 1-hydroxypyridine-2(1H)-thione or a pharmaceutically acceptable salt thereof, and (b) an antibacterial agent or a pharmaceutically In cases where compounds described herein are sufficiently basic or acidic, a salt of the compound can be useful as an intermediate for isolating or purifying a compound described herein. Additionally, administration of a compound described herein as a pharmaceutically acceptable acid or base salt may be appropriate. As used herein, the term "pharmaceutically acceptable salts" is meant to include salts of the active compounds which are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The compounds described herein can be formulated as pharmaceutical compositions and administered to a mammalian host, such as a human patient in a variety of forms adapted to the chosen route of administration, i.e., orally or parenterally, by intravenous, intramuscular, topical or subcutaneous routes. In one embodiment the compounds described herein can be administered to the mammal (e.g., human patient) as a prodrug of the compound.

Thus, the compounds described herein may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds described herein may be applied in pure form, i.e., when they are liquids. However, the compounds described can also be administered to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds described herein to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949. The amount of the compounds, or an active salts or derivatives thereof, required for use in treatment will vary not only with the particular salt selected but also with the route of administration, the nature of the condition being treated and the age and condition of the patient and will be ultimately at the discretion of the attendant physician or clinician. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The compounds described herein can be conveniently formulated in unit dosage form; for example, containing 5 to 1000 mg, or 10 to 750 mg, or 50 to 500 mg of active ingredient per unit dosage form. In one embodiment, the invention provides a composition comprising a compound described herein formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In some embodiments, one or more of the compounds described herein are co-administered. Co-administration of the compounds described herein (optionally with one or more other active therapeutic agents) generally refers to simultaneous or sequential administration of a compound described herein. In one embodiment therapeutically effective amounts of the compounds co-administered are present in the body of the patient.

In some embodiments, one or more of the compounds disclosed herein are co-administered by combining the compounds disclosed herein in a unitary dosage form for simultaneous or sequential administration to a patient. Thus, this combination therapy may be administered as a simultaneous or sequential regimen. When administered sequentially, the combination may be administered in two or more administrations.

The invention will now be illustrated by the following non-limiting Examples.

EXAMPLE 1

Materials and Methods

Materials

L-captopril, SAHA and pyrithione salts (2) were commercially purchased from Sigma Aldrich. Compounds 3-5 were obtained following literature procedures (R. Muthyala, et al., Bioorganic & medicinal chemistry letters, 25 (2015) 4320-4324; R. Muthyala, et al., Bioorganic & medicinal chemistry letters, 24 (2014) 2535-2538). Compound 1 was obtained from an in-house unpublished library and was included as a comparison compound to hydroxamic acid and 1,2-HPT. For the synthesis of 1, all chemicals were purchased from commercial suppliers and used as received unless otherwise stated. Flash silica gel chromatography was performed using standard commercial source (40-60 μm mesh). Inert reactions were carried out under nitrogen atmosphere (balloon), $H^1$ NMR spectra were recorded at ambient temperature on a 300 MHz Varian FT-NMR instrument.

Synthesis

Methyl 6-chloronicotinate (7)

To a cooled (0° C.) solution of 6-chloronicotinic acid 6 (200 mg, 1.29 mmol) in $CH_2Cl_2$ (5 mL), 2 drops of DMF and oxalyl Chloride (0.13 mL, 1.52 mmol) was added drop wise. The reaction mixture was stirred at room temperature for 16 h and the volatiles were removed under reduced pressure. The residue was cooled to 0° C. and dissolved in $CH_2Cl_2$ (5 mL), methanol (1 mL) and heated to 40° C. (monitored by TLC). After 15 min, the solvents were removed under vacuo, diluted with ether. The organic layer was washed with water and brine solution. The organic extracts were dried over anhydrous $Na_2SO_4$ and concentrated under reduced pressure, to afford methyl 6-chloronicotinate 7 (200 mg, 91%) as off-white solid. $^1H$ NMR (400 MHz, $CDCl_3$): δ 9.00 (s, 1H), 8.26 (d, J=8.4 Hz, 1H), 7.43 (d, J=8.4 Hz, 1H), 3.96 (s, 3H).

Methyl 6-chloropyridine-3-carboxylate-1-oxide (8)

To the suspension of methyl 6-chloronicotinate 7 (200 mg, 1.14 mmol)) and urea hydrogen peroxide (230 mg, 2.44 mmol) in $CH_3CN$ at 0° C., trifluoroacetic anhydride (0.35 mL, 2.33 mmol) was added drop wise and stirred at room temperature for 16 h. The reaction was monitored with TLC; volatiles were concentrated under reduced pressure. The residue was partitioned between EtOAc (10 mL) and saturated sodium hydrogen sulfite (10 mL). The aqueous layer was extracted with EtOAc (2×10 mL). The combined organic extracts were washed with brine solution, dried over anhydrous $Na_2SO_4$ and concentrated under reduced pressure to give crude methyl-6-chloropyridine-3-carboxylate-1-oxide 8 which was carried forward to next step without any further purification. $^1H$ NMR (500 MHz, DMSO-d6): δ 8.73 (s, 1H), 7.95 (d, J=8.5 Hz, 1H), 7.76 (d, J=8.5 Hz, 1H), 3.89 (s, 3H).

Methyl-1-hydroxy-6-oxo-1,6-dihydropyridine-3-carboxylate (9)

To the crude methyl-6-chloropyridine-3-carboxylate-1-oxide 8 (50 mg, 0.26 mmol) in $CH_3CN$ (2 mL), trifluoro acetic anhydride (2 mL) was added dropwise and stirred at room temperature. The reaction was monitored with TLC. After 1 h, the volatiles were removed under reduced pressure. Solid sodium bicarbonate (100 mg) and MeOH (10 mL) was added to the residue and the suspension was filtered. The filtrate was concentrated under reduced pressure to provide the crude methyl-1-hydroxy-6-oxo-1,6-dihydropyridine-3-carboxylate 9 which was taken to the next step without any further purification. $^1H$ NMR (400 MHz, $CD_3OD$): δ 8.56 (s, 1H), 7.87 (d, J=8.8 Hz, 4H), 6.64 (d, J=8.8 Hz, 4H), 3.85 (s, 3H).

Methyl 1-(benzyloxy)-6-oxo-1,6-dihydropyridine-3-carboxylate (10)

To a stirred solution of methyl-1-hydroxy-6-oxo-1,6-dihydropyridine-3-carboxylate 9 (800 mg, 5.26 mmol), $K_2CO_3$ (2.1 gm, 15.6 mmol) in DMF (2 mL) at 0° C., benzyl bromide (0.75 mL, 6.3 mmol) was added drop-wise and stirred at room temperature for 16 h. The reaction mixture was diluted with cold water (15 mL) and extracted with EtOAc (3×5 mL). The combined organic extracts were washed with water and brine solution, dried over anhydrous $Na_2SO_4$ and concentrated under reduced pressure. The residue was purified with silica gel (60-120 mesh) column chromatography (20% EtOAc-hexane) to afford methyl 1-(benzyloxy)-6-oxo-1,6-dihydropyridine-3-carboxylate (410 mg, 38.6% after 3 steps) as a solid. $^1H$ NMR (500 MHz, $CD_3OD$): δ 8.22 (s, 1H), 7.9 (d, J=9.5 Hz, 1H), 7.47-7.45 (m, 2H), 7.39-7.31 (m, 3H), 6.67 (d, J=9.5 Hz, 4H) 5.28 (s, 2H), 3.79 (s, 3H).

1-(Benzyloxy)-6-oxo-1,6-dihydropyridine-3-carboxylic acid (11)

To compound 5 (3.2 gm, 12.35 mmol) dissolved in MeOH (30 mL) at 0° C., 1N NaOH (25 mL, 24.7 mmol) was added and stirred at room temperature for 16 h. The volatiles were concentrated under reduced pressure to give the residue which was acidified with 8N HCl during which solid was precipitated. The solid was filtered, washed with water and dried under vacuum to afford 1-(benzyloxy)-6-oxo-1,6-dihydropyridine-3-carboxylic acid 11 (2.08 gm, 66%) as a solid. $^1H$ NMR (400 MHz, $CD_3OD$): δ 8.18 (s, 1H), 7.91 (d, J=9.6 Hz, 1H), 7.47-7.45 (m, 2H), 7.40-7.38 (m, 3H), 6.67 (d, J=9.6 Hz, 4H) 5.29 (s, 2H).

Methyl 2-(1-(benzyloxy)-6-oxo-1,6-dihydropyridine-3-carboxamido)-2-phenylacetate (13)

A mixture of 1-(benzyloxy)-6-oxo-1,6-dihydropyridine-3-carboxylic acid 11 (1.6 g, 6.53 mmol) (R)-methyl 2-amino-2-phenylacetate hydrochloride 12 (1.3 g, 6.53 mmol), EDC.HCl (1.5 g, 7.82 mmol), HOBt (1.05 g, 7.83 mmol) and DIPEA (2.5 mL, 15.06 mmol) in DMF (10 mL) was stirred at room temperature for 6 h. The mixture was diluted with water (30 mL) and extracted with EtOAc (3×20 mL), combined organic extracts were washed with brine, dried over $Na_2SO_4$ and concentrated under reduced pressure to give the crude residue. The residue was purified by column chromatography on silica gel (60-120) with 2% MeOH/$CH_2Cl_2$ as an eluent to furnish methyl 2-(1-(benzyloxy)-6-oxo-1,6-dihydropyridine-3-carboxamido)-2-phenylacetate 13 (1.5 g, 62.5%) as a solid. $^1$H NMR (400 MHz, $CDCl_3$): δ 7.83 (s, 1H), 7.63 (d, J=6.8 Hz, 1H), 7.43-7.31 (m, 10H), 6.67-6.65 (m, 2H), 5.62 (d, J=9.6 Hz, 1H), 5.27 (s, 2H), 3.75 (s, 3H).

2-(1-(Benzyloxy)-6-oxo-1,6-dihydropyridine-3-carboxamido)-2-phenylacetic acid (14)

To a stirred solution of methyl 2-(1-(benzyloxy)-6-oxo-1,6-dihydropyridine-3-carboxamido)-2-phenylacetate 13 (500 mg, 1.27 mmol) in THF:MeOH (1:1, 5 mL), 5% LiOH (5 mL, W/V) solution was added slowly and stirred at room temperature for 16 h, solvent was concentrated under reduced pressure. The residue was cooled to 0° C. and acidified with 1N HCl and extracted with 10% MeOH in $CH_2Cl_2$ (3×20 mL). The combined organic extracts were washed with saturated brine solution, dried over Na2SO4 and concentrated to obtain 2-(1-(benzyloxy)-6-oxo-1,6-dihydropyridine-3-carboxamido)-2-phenylacetic acid 14 (230 mg, 48%) as an off-white fluffy solid. 1H NMR (400 MHz, CD3OD): δ 8.33 (s, 1H), 7.94 (d J=6.8 Hz, 1H), 7.48-7.32 (m, 11H), 6.68 (d, J=9.6 Hz, 1H), 5.53 (s, 1H), 5.27 (s, 2H).

2-(1-Hydroxy-6-oxo-1,6-dihydropyridine-3-carboxamido)-2-phenylacetic acid (1)

To 2-(1-(benzyloxy)-6-oxo-1,6-dihydropyridine-3-carboxamido)-2-phenylacetic acid 14 (3 g, 7.93 mmol) dissolved in 1,4-Dioxane (300 mL), 10% Pd/C (300 mg) was added portion wise and stirred under hydrogen atmosphere for 8 h. The reaction was monitored with TLC. The catalyst was filtered through celite bed and concentrated. The crude residue was purified using chiral HPLC, to obtain 1 (racemic, 700 mg, 23%) as an off-white solid. 1H NMR (400 MHz, CD3OD): δ 8.57 (s, 1H), 7.99 (d, J=6.8 Hz, 1H), 7.51-7.49 (m, 2H), 7.43-7.37 (m, 3H), 6.66 (d, J=9.6 Hz, 1H), 5.64 (s, 3H).

Protein Expression and Purification

For our biochemical assay, the blavmugene, from a clinical strain of *P. aeruginosa*, was expressed using the pET24a (+) vector [20]. The pET24a-VIM-2 plasmid was transformed into competent BL21 (DE3) *E. coli* cells. The cells were plated onto an LB-agar plate with kanamycin (25 µg/mL) and incubated overnight at 37° C. A single colony was used to inoculate 50 mL of LB, containing 25 µg/mL kanamycin, and the culture was shaken overnight at 37° C. From the overnight culture, 10 mL were transferred to 4×1 L LB medium containing 25 µg/mL kanamycin. The cultures were grown at 37° C. until the optical density ($OD_{600\ nm}$) reached 0.6-0.8, at which point protein production was induced with IPTG (0.5 mM) and ZnCl2 (100 µM). The temperature was reduced to 20° C., and the cells were shaken for an additional 18 h. The cultures were harvested by centrifugation (8K×g) for 10 min at 4° C. The resulting pellets were re-suspended with 25 mL of 50 mM HEPES, pH 7.5, containing 500 mM NaCl (buffer B). The cells were lysed with three passes through a French Press. The lysate was centrifuged (15 Kxg) for 30 min at 4° C. The supernatant was dialyzed against 2 L of 50 mM HEPES, pH 7.5 (buffer A), for 4 h. Buffer A was used to equilibrate a 25 mL Q-Sepharose column using an FPLC. The sample was loaded onto the column, and proteins were eluted with a linear gradient 0-500 mM NaCl with buffer B. Fractions containing VIM2, determined by SDS-PAGE, were pooled and concentrated to 2-3 mL in an Amicon ultraconcentrator equipped YM-10 membrane. Further purification was conducted with a Sephacryl S-200 gel filtration column using 50 mM HEPES, pH 7.5, containing 150 mM NaCl. Fractions containing pure VIM2 were pooled, and metal analysis was performed (M. Aitha, A et al., Biochemistry-Us, 53 (2014) 7321-7331).

Biochemical Assay

Nitrocefin (Cayman, CAS 41906-86-9) was used as the chromogenic substrate for all biochemical assay. The enzymatic activity of purified VIM2 was determined spectrophotometrically (spectramax-M5-reader) at room temperature in 50 mM potassium phosphate buffer at pH 7.0. The rate of product formation was monitored based on the $\lambda_{max}$=486 nm absorbance taken at 10 s intervals for 30 mins. The $K_m$ and $k_{cat}$ values were determined from 10 different concentrations of nitrocefin ranging from 0.001 to 100 µM with at least four independent initial-velocity measurements and fitted by nonlinear regression using Michaelis-Menten Enzyme kinetics with Graphpad Prism 6.

Single Dose Enzymatic Inhibition Assay

To identify potential MBL inhibitors, the relative change in the formation of hydrolyzed nitrocefin between treated and untreated VIM2 was determined as percentage inhibition. 5 nM VIM-2 was pre-incubated for 10 mins with 50 µM of each compound, followed by the addition of 10 µM nitrocefin. The relative change in the $\lambda_{max}$=486 nm absorbance after 30 mins was evaluated as percentage inhibition.

Dose Response Enzymatic Inhibition Assay and Inhibition Constant

Each inhibitors was pre-incubated at concentrations from 0.001 to 50 µM with 5 nM VIM-2 for 5 mins at room temperature in detergent buffer before addition of 10 µM nitrocefin. The rate of product formation was monitored based on the $\lambda_{max}$=486 nm absorbance taken at 10 s intervals for 30 mins. The relative change in absorbance was evaluated as percentage inhibition and the IC50 was determined by fitting the data to a sigmoidal dose-response curve. The enzyme inhibition constant (Ki) was derived from initial-velocity measurements by nonlinear regression using competitive-inhibition enzyme kinetics using Graphpad Prism 6.

Bacteria Cell Culture

Both the native and transformed cells lines have been reported previously (L. Borgianni, et al., Antimicrob Agents Ch, 54 (2010) 3197-3204). The cells were cultured on 0.8 g/100 ml nutrient agar plate at pH 7.0 and 37° C. The bacterial growth medium was diluted in nutrient broth (NB) to a concentration absorbance of 1.5 at $OD_{600\ nm}$ and incubated overnight in 10 ml capped culture tubes with shaking. An overnight culture of the bacterial strain was sub-cultured to an optical density of 0.06 at $OD_{600\ nm}$ into the NB medium and was then seeded at max 200 µl into the wells of a 96 well microtiter plate. Samples were then incubated at 37° C. and shaken at 200 rpm for 18 h. The absorbance was measured on an ELIZA plate reader at 600 nm and analyzed with the Gen5™ software suite (version 1.08).

Half Maximal Effective Concentration ($EG_{50}$)

The bacterial culture was prepared as described above. The diluted subculture bacteria in NB medium was then set up to a final volume of 200 µl in clear flat-bottom 96-well plates containing ten different concentrations of each tested compound ranging from 0.001 µM to 50 µM. The mixing of the bacterial culture plate were then incubated in a 37° C. stationary shaken incubator at 200 rpm for 18 h before measuring their optical density at 600 nm. The EC50 were obtained by fitting the data to a sigmoidal dose-response equation using Graphpad Prism 6.

Human Cell Line Culture

Human embryonic kidney cell line (HEK293) was grown in DMEM (Dulbecco's modifications of eagle's medium with L-glutamine & 4.5 G/L glucose) supplemented with fetal bovine serum 100 units/ml of penicillin G and 0.1 mg/ml of streptomycin sulfate in a humidified atmosphere of a 5% $CO_2$ at 37° C.

Cell Proliferation Assays

Cell proliferations were measured by counting viable cells by using the 3(4,5dimethylthiazol-2-yl)-2,5-diphenyltetrazolium bromide (MTT) (Sigma-Aldrich, St. Louis, Mo.) colorimetric dye-reduction assay. RPMI-1640 Gibco® (10% FBS, 2 mM L-glutamine, 1 mM pyruvate, 1% penicillin/streptomycin) growth media were used and the cells were seeded at a concentration of 1×104 cells/well in 200 µl culture medium and incubated at 37° C. in 5% $CO_2$ incubator. After 72 hrs, 10 µl of MTT (5 mg/ml) dye was added to each well and the plates were incubated for 4 hours at 37° C. in 5% $CO_2$ incubator. After centrifuge with 1,500 rpm/10 mins, the supernatant was removed and 200 µl of dimethyl sulfoxide (DMSO) was added and the plates were gently shaken to solubilize the formed formazan for 30 min. The absorbance was measured using a micro-plate reader at wave length 590 nm. The CC50 were obtained by fitting the data to a sigmoidal dose-response equation using Graphpad Prism 6.

Molecular Modeling

All modeling was performed using the Schrodinger modeling package (N.Y. Schrodinger LLC, NY, Maestro v9.7, Bioluminate v1.2, Canvas v1.9, Epik v2.7, Glide v6.2, LigPrep v2.9, MacromModel v10.3, Prime v3.5, Schrodinger LLC, New York, N.Y., in, 2014). The modeling study was based on the X-ray crystallographic structures of VIM2 (PDB code: 4NQ2, 4BZ3, 4C1E). All missing sidechains and hydrogen atoms were added with standard protein preparation protocols at physiological pH, followed by energy minimization using OPLS-AA 2005 force field with implicit solvent to optimize all hydrogen-bonding networks.

Results and Discussion

The synthesis of compound 1 is shown in Scheme 1. It begins with 6-chloropyridine 3-carboxylic acid 6. The N-oxidation with $H_2O_2$ in trifluoro acetic acid anhydride (TFAA) did not lead to completion of the reaction; substantial amount of starting material was left even after addition of additional 2-3 equivalent of hydrogen peroxide. Further, separation of N-oxide from starting acid was not optimized. Instead, the synthesis started with methyl ester of 7. The N-oxidation was carried out using urea-hydrogen peroxide addition complex in trifluoro acetic acid anhydride (M. Ando, N et al., Bioorgan Med Chem, 17 (2009) 6106-6122). The 6-chloro N-oxide 8 was converted into 6-oxo compound 9 using TFAA keeping the carboxylic acid ester intact. This was then benzylated with benzyl bromide in the presence of potassium carbonate. The methyl ester of N-benzyl compound 10 was hydrolyzed with NaOH in methanol. Initially coupling with (R) methyl 2-amino-2-phenylacetate hydrochloride 12 was tried under variety of peptide coupling condition. Racemization occurred in almost all cases and in addition gave low yields after chromatography. Although racemization coupling with the reagent combination-EDC, HOBt and DIPEA in DMF gave good yields. Attempts to debenzylate with Pd/C/$H_2$ were unsuccessful; for most all conditions the benzyloxy group was cleaved leaving 6-hydroxy pyridine derivative. However, first hydrolyzing the ester to carboxylic acid with LiOH followed by hydrogenation, gave the desired compound 1 in acceptable yields with 80% enantiomer excess (chiral HPLC).

Scheme 1: Synthesis of compound 1

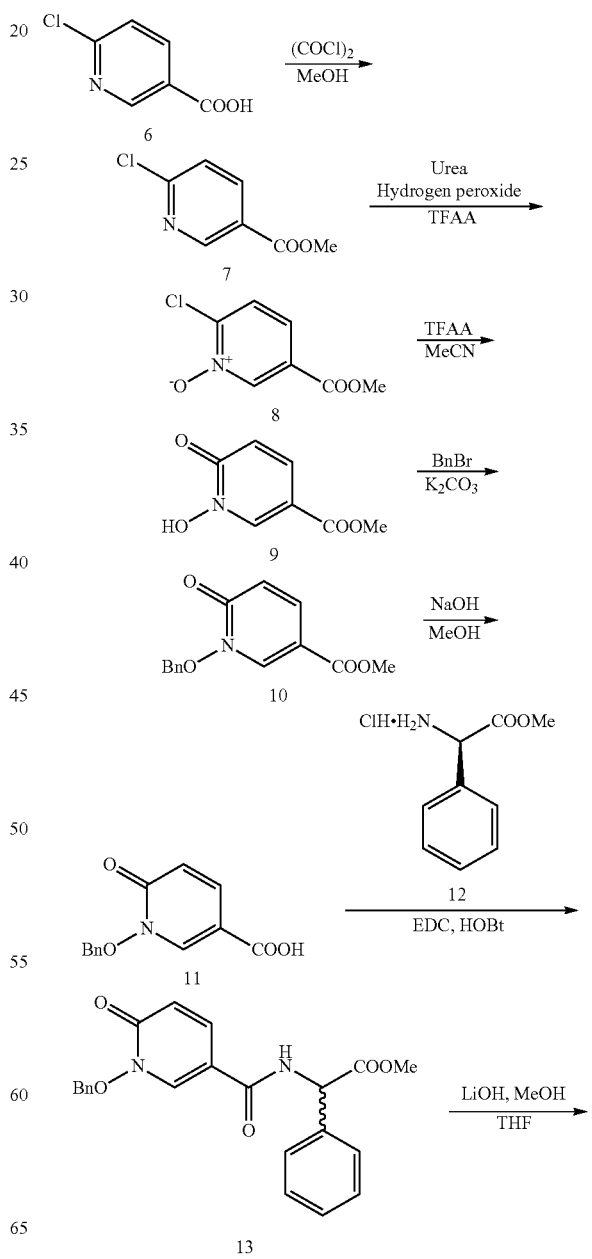

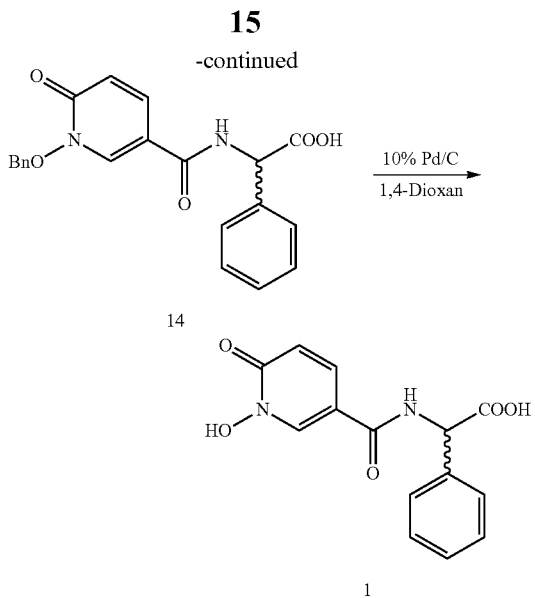

Figure 2:
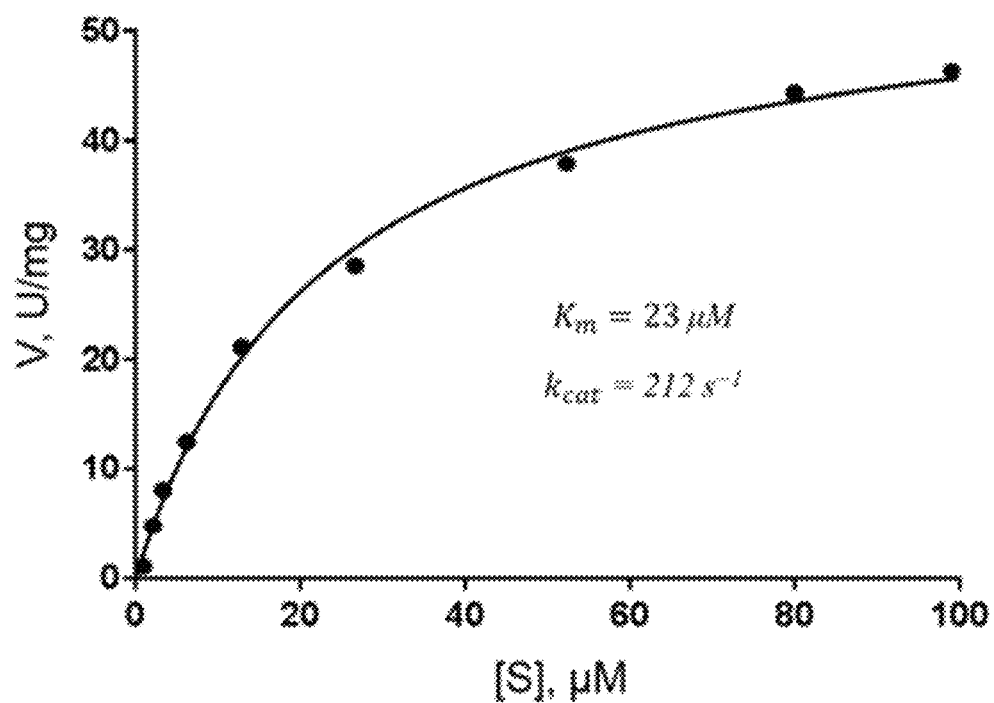
FIG. 2 illustrates the steady-state kinetics for the hydrolysis of nitrocefin by VIM-2.

FIG. 2 shows Steady-state kinetics for the hydrolysis of nitrocefin by VIM-2. The determined $K_m$ and $k_{cat}$ was 23.0 μM and 212 s$^{-1}$, respectively, comparable to literature (P. Marchiaro, P. E. et al., Antimicrob Agents Ch, 52 (2008) 2250-2252). As shown in Table 1, both clavunalate and tazobactam, two of the FDA approved β-lactamase inhibitors, were included as control for the preliminary single dose inhibition assay screening, with neither compounds exhibiting more that 25% inhibition against VIM2. Both compound 3 and L-captopril exhibit a remarkable 98% VIM2 inhibition. Poor inhibition was observed for SAHA and compound 1, suggesting both hydroxamic acid and cyclic hydroxamic acid as poor starting pharmacophore for MBLi design. Interestingly, 1,2-HPT from zinc pyrithione salt showed relatively weak inhibition activity of 15% as compared to sodium pyrithione salt which has a comparable inhibition activity of 93% to compound 3. This difference is likely a result of available unchelated 1,2-HPT for VIM2 inhibition. Moderate inhibitory activities were also observed for 4 and 5 between the methyl and phenyl substitution, indicating inhibitory affinity can be enhanced by the addition of aromatic ring at the non-zinc binding group.

TABLE 1

Single dose inhibition assay against VIM2

| Compound | % Inhibition at 50 μM |
|---|---|
| L-Captopril | 98 |
| Clavulanate | 15 |
| Tazobactam | 25 |
| SAHA | 29 |
| 1 | 12 |
| 2a (zinc salt) | 15 |
| 2b (sodium salt) | 93 |
| 3 | 98 |
| 4 | 18 |
| 5 | 34 |

The IC50 and inhibitory constant, $K_i$, for the four compounds with the highest single dose VIM2 inhibition were determined and are shown in Table 2. The determined IC50 for L-captopril was 6.6 μM and was comparable to earlier report (J. Brem, et al., Antimicrob Agents Chemother, 60 (2016) 142-150). Its $K_i$ was 630 nM corresponding to a ligand efficiency (LE) of 0.51. For compound 2b (sodium salt), the determined IC50 and $K_i$ were 908 nM and 217 nM, respectively, resulting in a remarkable LE of 1.15 and is likely the highest ever determined for a reported MBLi. For compound 3, which has been shown as a selective HDAC inhibitor in our earlier study (R. Muthyala, et al., Bioorganic & medicinal chemistry letters, 25 (2015) 4320-4324) the determined IC50 and $K_i$ were 270 nM and 13 nM, respectively, which corresponds to a 0.99 LE. Incorporation of a single amino acid with phenyl sidechain, 5, significantly diminishes its $K_i$ by 576-fold from 0.013 nM to 7.5 μM. Given the observed data from the biochemical assays, the 20-fold enhanced potency by the addition of the carboxylic acid group adjacent to the N1 position of compound 2b is likely due to its electronic effect on 1,2-HPT zinc binding affinity, a perturbation to the 1,2-HPT $pK_a$, and its interaction with nearby residues within the active site. Removal of the carboxylic acid from the adjacent N1 position of compound 3 or its separation by three atom spacer through amino acid addition could explain the significant of loss of inhibition potency in 4 and 5.

TABLE 2

Inhibitory activity against VIM2

| Compound | $K_i$ (μM) | IC50 (μM) | LE |
|---|---|---|---|
| L-Captopril | 0.63 | 6.6 (4.4) | 0.51 |
| 2b | 0.217 | 0.908 | 1.15 |
| 3 | 0.013 | 0.27 | 0.99 |
| 5 | 7.5 | 67.9 | 0.34 |

Ligand efficiency (LE) = −1.38 log (Ki)/N where N = number of heavy atoms.
IC50 in parenthesis reported from ref. 3.

Figure 3A:
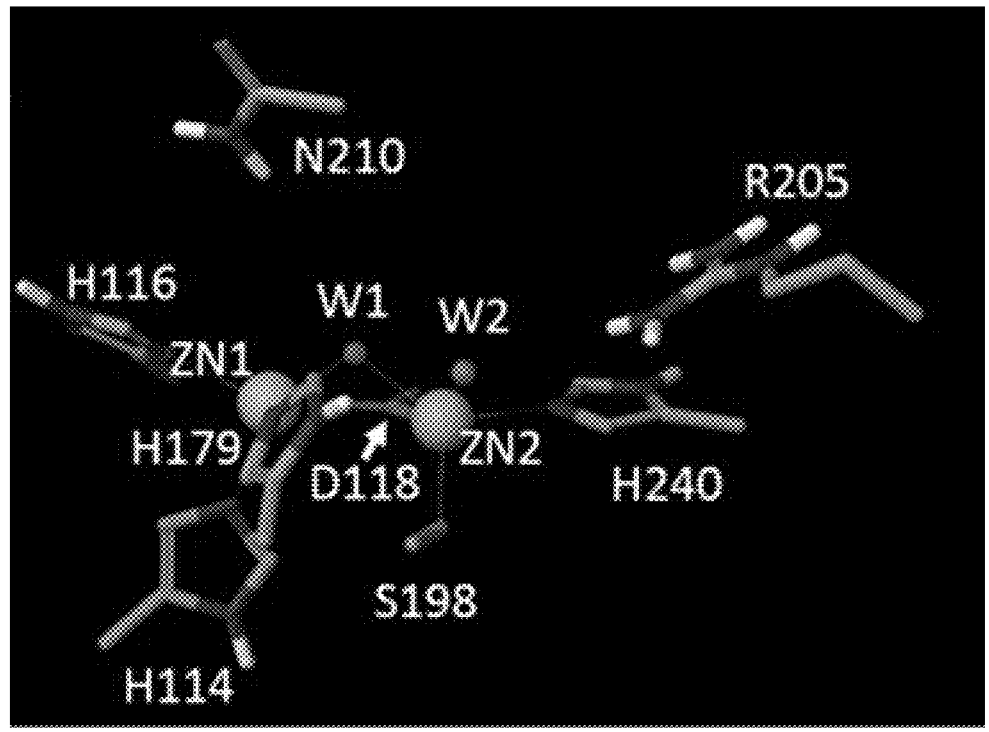
FIGS. 3A, 3B, 3C and 3D illustrate the VIM2 active site; (3A) without ligand (4NQ2), (3B) with formic acid (4BZ3), (3C) with D-captopril (4C1E) and (4D) with model compound 3. The chelated waters are labeled as W1 and W2.
Figure 3B:
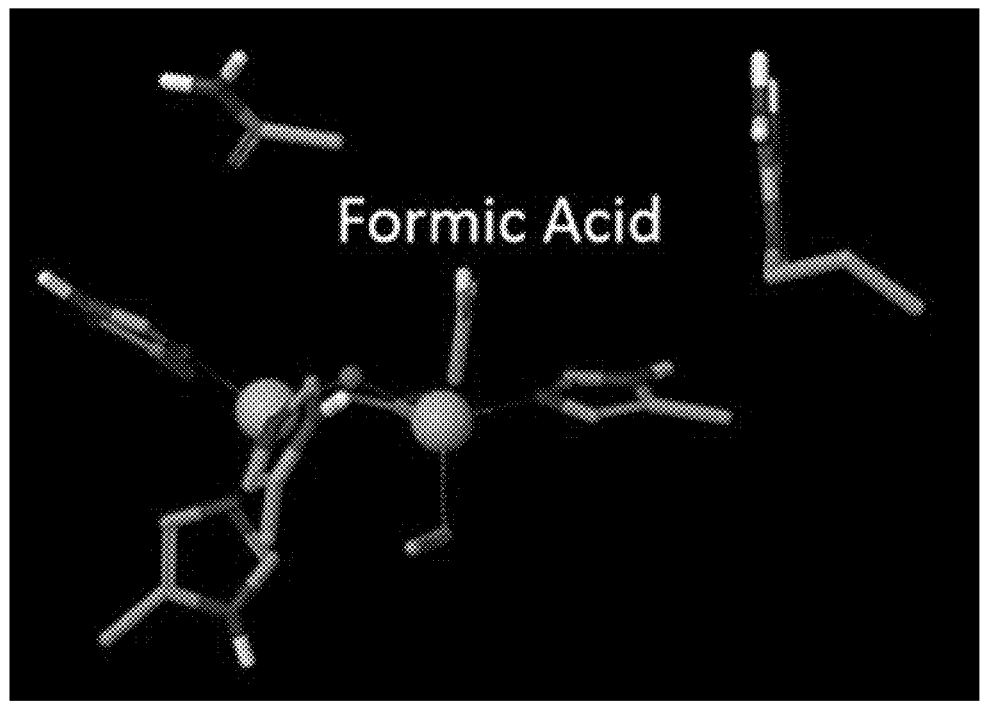
Figure 3C:
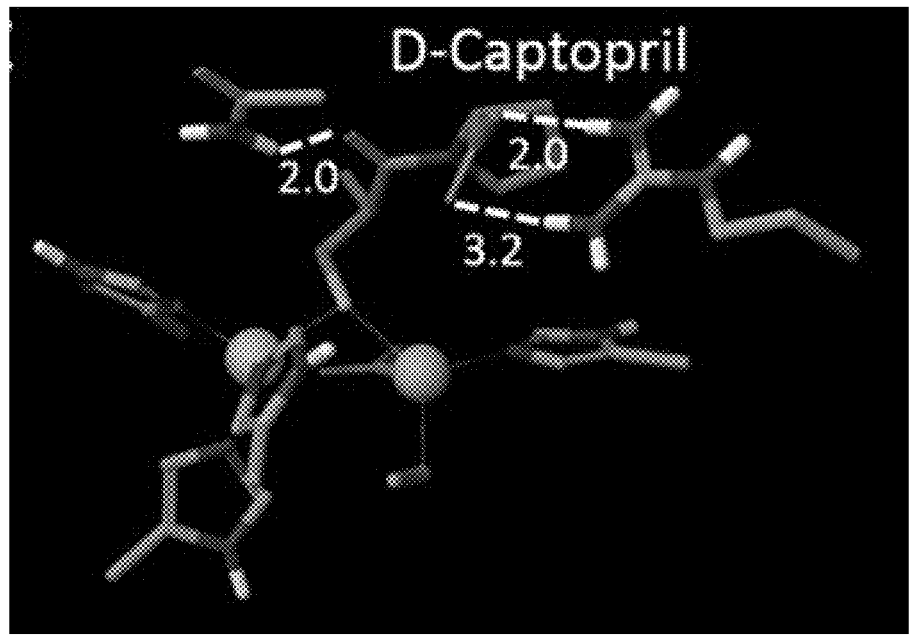
Figure 3D:
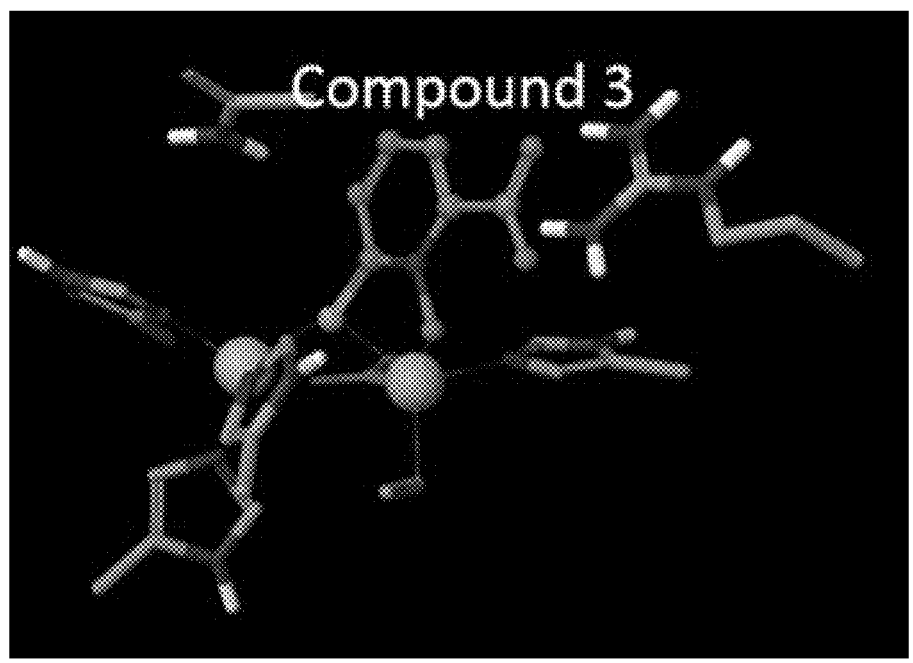
Figure 4:
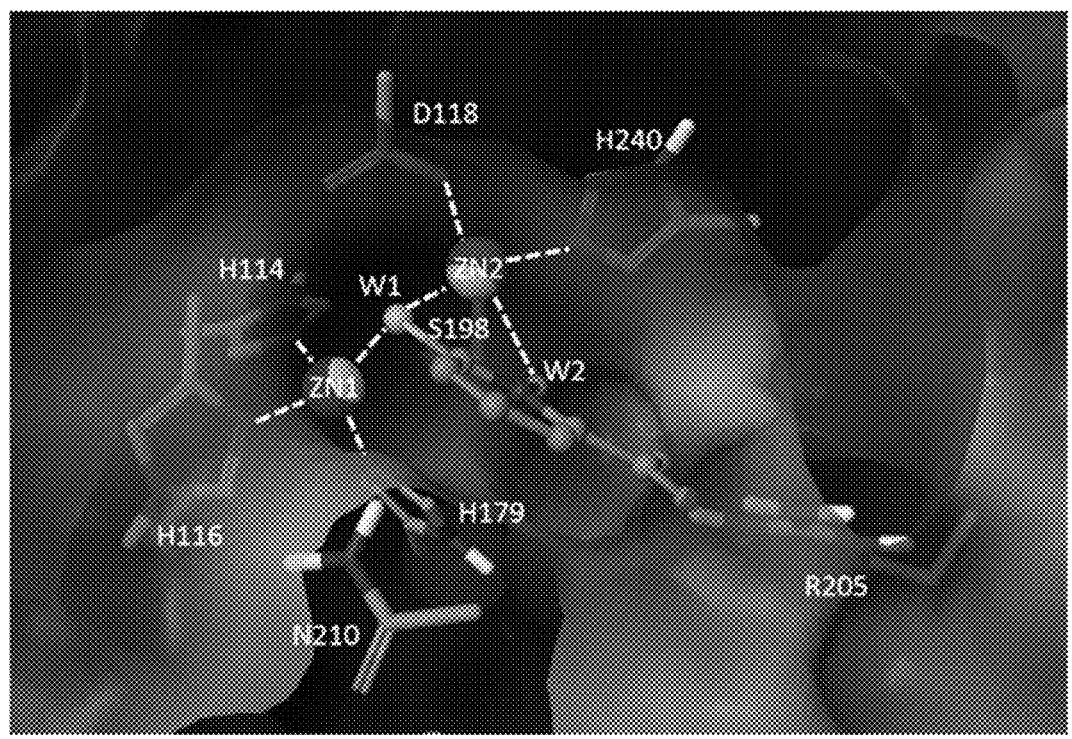
FIG. 4 illustrates the top view of VIM2 binding site with compound 3 with its sulfur and oxygen atom chelating to ZN1 and ZN2 at the W1 and W2 water sites.

Numerous structural studies of VIM2 have been carried out to examine the exact mechanism of ligand binding for various well-establish MBLi's (J. Brem, et al., Antimicrob Agents Chemother, 60 (2016) 142-150; M. Aitha, A et al., Biochemistry-Us, 53 (2014) 7321-7331). To better understand the mechanism of MBL binding, the previously solved X-ray structures complexes of VIM2 were examined. As shown in FIG. 3A, in the absence of ligands, two water molecules (W1 and W2) with W1 acting as a bridge chelate between the two Zn1 and Zn2 ions. Zn1 is in tetra-coordinated to H114, H116, H179 and W1 while Zn2 is in penta-coordinated to D118, S198, H240, W1 and W2. The carboxylates of formic acid displaces W2 from Zn2 while the thiolate ion of D-captopril replaces W1 as the bridging chelate (FIG. 3B). D-captopril also undergoes hydrogen bonding to the amide hydrogen of N210 sidechain and forms a direct salt bridge with R205 (FIG. 3C). Cross examination with other available MBLs (PDB: 1DD6, 3VQZ, 2QDT, 2FU9) with bound ligands consistently showed thiolate as the preferred as the bridging chelate over carboxylate when both are present. Given the fact that pyrithione can undergo resonance state to form thiolate ion, the expected mode of binding involve thiolate ion as the bridging chelating-atom between the two zinc ions (FIG. 3D).

To improve the understanding of potential mode of binding for 3, molecular modeling was carried out using Schrodinger modeling suites (N.Y. Schrodinger LLC, NY, Maestro v9.7, Bioluminate v1.2, Canvas v1.9, Epik v2.7, Glide v6.2, LigPrep v2.9, MacromModel v10.3, Prime v3.5, Schrodinger LLC, New York, N.Y., in, 2014). Docking with Glide into metallo enzymes did not reliably reproduce the structurally observed mode of binding with observed sulfur atoms acting as a bridge chelate between the two zinc ions (unpublished). Due to the presence of the charged carboxylate group, the dominant pose observed involved chelation of the carboxylate to the zinc ions. As such, comparative modeling based on established structurally determined mode of binding was carried out to yield the most consistent model to corroborate with our biochemical data (FIG. 3D). The model of 3 binding to VIM2 was developed through overlaying of the chelating S and O atoms from 1,2-HPT moiety and its carboxylate group to the two crystallographic water sites (W1 and W2) and D-captopril's carboxylate group. Such model would preserve the commonly observed mode of thiolate ligand binding with the sulfur acting as the chelating atom for bridging the two zinc ions for VIM2 binding. This model also consistently replaces the other chelating water atom, W2, and preserves the salt bridge interaction with R205. As D-Captopril's salt bridge interaction with Lys does not yield nanomolar inhibition in IMP1 and BcII, this mode of binding would corroborate with the observed nanomolar inhibitory activity of D-captopril that is not achieved in BcII and IMP1. The removal of the carboxylic acid would lead to the loss of the salt bridge interaction to R205 which would explain the 20-fold loss of the Ki for compound 2. Furthermore, this potential mode of binding will likely restrict the placement of the amino acid group at the D-captopril carboxylate site leading to significant loss in binding affinity to the active site as observed in 5.

The clinical relevance of compound 3 was further demonstrated by its ability to restore amoxicillin efficacy against VIM2 expressing *E. coli*. Clavulanate was included as control. As shown in Table 3, the growth of wild type *E. coli* can be effectively inhibited by 50 μM of amoxicillin regardless of the presence of the MBLi. The transformation and expression of VIM2 MBL leads to amoxicillin resistance in *E. coli*, rendering the treatment with amoxicillin alone and the amoxicillin—clavulanic acid combination therapy ineffective. Compound 2 which has a Ki of 217 nM exhibits potent antibacterial activity against both *E. coli* strains with over 89% growth inhibition activity on its own, making it unsuitable as a β-lactamase inhibitor for combination antibacterial therapy. For L-captopril and 3, both compounds exhibit only moderate antibacterial activity on their own against both wild type and VIM2 expressing *E. coli*. As nanomolar inhibitors, both compounds effectively inhibit VIM2 and restores amoxicillin efficacy with over 90% synergistic growth inhibition against VIM2 expressing *E. coli*.

TABLE 3

Cell viability assay

| Compound | *E. coli* | | VIM2 expressing *E. coli* | |
| --- | --- | --- | --- | --- |
| | Amox(−) | Amox(+) | Amox(−) | Amox(+) |
| Amox | — | 3.6 | — | 77 |
| Clav | 86 | 2.9 | 93 | 57 |
| SAHA | 83 | 3.6 | 79 | 60 |
| L-Captopril | 86 | 5.0 | 87 | 9.3 |
| 2b | 5.3 | 1.9 | 11 | 2.1 |
| 3 | 77 | 3.6 | 61 | 3.2 |

The data are reported as relative percentage growth compared to untreated cells.

Since β-lactamase inhibitors serve primarily as a β-lactam antibiotic re-activating agents, β-lactamase inhibitors commonly do not exhibit sufficient antibacterial activity on their own. To evaluate its therapeutic potential, it is important to examine its efficacy in the presence of a β-lactam antibiotic. The effective β-lactamase inhibitor concentration in which a fixed concentration of antibiotic regains 50% of its growth inhibitory activities (EC50*) was evaluated. Such an approach would avoid the immediate need to determine an optimal combination index necessary for future formulation studies and allow the direct comparison between two potential β-lactamase inhibitor candidates. As the growth of the wild type *E. coli* can be effectively inhibited at over 96% by amoxicillin alone at 50 μM, the EC50* for 3 and L-captopril was determined under the same condition against VIM-2 expressing *E. coli*. The determined EC50* was 0.10 uM for 3 and 1.7 uM for L-captopril (Table 4) which corresponds to a 2 to 10 fold change from its observed Ki.

TABLE 4

Cell bioactivities

| Compound | CC50 (μM) | EC50* (μM) | TI |
| --- | --- | --- | --- |
| L-Captopril | — | 1.7 | — |
| 2b | 0.014 | — | — |
| 3 | 97 | 0.110 | 880 |

*the EC50* of 3 was determined in the presence of 50 μM amoxicillin.
Therapeutic index (TI) = CC50/IC50.

To determine the overall therapeutic index of these two compounds, their cytotoxicity against human embryonic kidney HEK 293 cell lines by MTT assay as described earlier (R. Muthyala, et al., Bioorganic & Medicinal Chemistry Letters, 24 (2014) 2535-2538) was assessed. The CC50 of 3 has been reported (R. Muthyala, (2014) 2535-2538). Compound 2 was included to compare the pharmacological difference for the addition of the carboxylic acid group at the 6″ position of 2. As 1,2 HPT (2) is known as a non-selective zinc chelating agent with a wide spectrum antimicrobial activities which was also observed here against both *E. coli* strains, our earlier study have demonstrated compound 3 is a selective HDAC inhibitor with nearly 5000-fold range selectivity among all eleven HDACs and may not possess the same therapeutic profile as the parent compound 2. As shown in Table 4, the determined CC50 for 2 and 3 after 72 hrs treatment against HEK293 cells was 0.014 uM and 97 uM. This modest modification resulted in an unexpected and remarkable 6900 fold change in cytotoxicity that further support 3 as a selective inhibitor that does not exhibit any reasonable high affinity for other biologically important zinc enzymes, a major concern in rational drug design. The determined TI for 3 was 880, giving it a promising starting therapeutic window for further development.

Thus, the inhibition activity of three representative classes of zinc specific chelators as potential MBL inhibitors, namely hydroxamic acid, cyclic hydroxamic acid and pyrithione (1,2 HPT) has been described herein. 1-Hydroxypyridine-2(1H)-thiones-6-carboxylic acid, 3, has been demonstrated to be a potent nanomolar inhibitor of VIM2 with a $K_i$ of 13 nM that corresponds to a remarkable 0.99 ligand efficiency. There was a 6900 fold change in cytotoxicity from its parent compound, 2, observed through the addition of a carboxylic acid group at the $6^{th}$ position of 1,2-HPT that suggested limited off target liability against other cellular zinc enzymes. The mode of binding for 3 was further assessed by molecular docking which corroborate with the observed biochemical activities. The binding of 3 involves the sulfur acting as a bridging chelating atom to the di-zinc ions while its carboxylate group forms a salt bridge interaction to R205.

What is claimed is:

1. A method for treating or preventing a bacterial infection in an animal comprising systemically administering to the animal (a) a 1-hydroxypyridine-2(1H)-thione-6-carboxylic acid of formula:

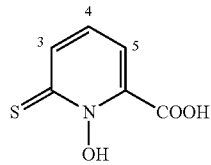

or a pharmaceutically acceptable salt thereof, and (b) an antibacterial agent or a pharmaceutically acceptable salt thereof.

2. The method of claim 1, wherein the antibacterial agent or a pharmaceutically acceptable salt thereof is a β-lactam antibiotic or a pharmaceutically acceptable salt thereof.

3. The method of claim 1, wherein the antibacterial agent or a pharmaceutically acceptable salt thereof is amoxicillin.

4. The method of claim 1, further comprising administering (c) one or more additional antibacterial agents or pharmaceutically acceptable salts thereof.

5. The method of claim 1, further comprising administering (c) one or more additional β-lactamase inhibitors or pharmaceutically acceptable salts thereof.

6. The method of claim 2, wherein the bacterial infection is a multi-drug resistant bacterial infection, and the 1 hydroxypyridine-2(1H)-thione-6-carboxylic acid or the pharmaceutically acceptable salt thereof restores the activity of the β-lactam antibiotic.

7. The method of claim 1, wherein the bacterial infection is caused by a pathogen that expresses a metallo β-lactamase and the 1 hydroxypyridine-2(1H)-thione-6-carboxylic acid or the pharmaceutically acceptable salt thereof is an inhibitor of the metallo β-lactamase.

8. The method of claim 1, wherein the bacterial infection is caused by a pathogen which overexpresses a metallo β-lactamase and the 1 hydroxypyridine-2(1H)-thione-6-carboxylic acid or the pharmaceutically acceptable salt thereof is an inhibitor of the metallo β-lactamase.

9. The method of claim 1, wherein the bacterial infection is caused by *Enterococcus faecium, Staphylococcus aureus, Klebsiella pneumoniae, Acinetobacter baumannii, Pseudomonas aeruginosa*, or an *Enterobacter* species.

10. The method of claim 9, wherein the bacterial infection is a multi-drug resistant bacterial infection.

11. The method of claim 10, wherein the multi-drug resistant bacterial infection is caused by a pathogen that expresses a metallo β-lactamase.

12. The method of claim 10, wherein the multi-drug resistant bacterial infection is caused by a pathogen which overexpresses a metallo β-lactamase.

13. The method of claim 1, wherein (a) and (b) are administered separately.

14. The method of claim 1, wherein the antibacterial agent is amoxicillin or a pharmaceutically acceptable salt thereof, and the bacterial infection is *Klebsiella pneumonia*.

15. A method for treating or preventing a multi-drug resistant bacterial infection in an animal comprising administering to the animal (a) 1-hydroxypyridine-2(1H)-thione-6-carboxylic acid or a pharmaceutically acceptable salt thereof, and (b) a β-lactam antibiotic or a pharmaceutically acceptable salt thereof, wherein the multi-drug resistant bacterial infection is caused by a pathogen that expresses a metallo β-lactamase.

16. The method of claim 15 wherein the β-lactam antibiotic or the pharmaceutically acceptable salt thereof is amoxicillin or a pharmaceutically acceptable salt thereof, and the activity of the β-lactam antibiotic is restored.

17. The method of claim 7, wherein the metallo β-lactamase is VIM-2.

18. The method of claim 15, wherein the metallo β-lactamase is VIM-2.

19. The method of claim 15, wherein 1-hydroxypyridine-2(1H)-thione-6-carboxylic acid is an inhibitor of the metallo β-lactamase.

20. The method of claim 1, wherein the 1-hydroxypyridine-2(1H)-thione-6-carboxylic acid or the pharmaceutically acceptable salt thereof is administered orally or intravenously.

\* \* \* \* \*